United States Patent
Keller

(10) Patent No.: US 8,167,835 B2
(45) Date of Patent: May 1, 2012

(54) SINGLE CHAMBER DEVICE FOR DRAWING IN AND DISPENSING COMPONENTS

(75) Inventor: Wilhelm A. Keller, Merlischachen (CH)

(73) Assignee: Medmix Systems AG, Rotkreuz (CH)

(*) Notice: Subject to any disclaimer, the term of this patent is extended or adjusted under 35 U.S.C. 154(b) by 0 days.

(21) Appl. No.: 12/866,885

(22) PCT Filed: Feb. 19, 2009

(86) PCT No.: PCT/CH2009/000070
§ 371 (c)(1),
(2), (4) Date: Aug. 9, 2010

(87) PCT Pub. No.: WO2009/105905
PCT Pub. Date: Sep. 3, 2009

(65) Prior Publication Data
US 2011/0004156 A1 Jan. 6, 2011

(30) Foreign Application Priority Data
Feb. 28, 2008 (CH) ........................... 0292/08

(51) Int. Cl.
*A61M 37/00* (2006.01)
(52) U.S. Cl. .......................... 604/89; 604/82
(58) Field of Classification Search .............. 604/82, 604/89–91; 606/92–95; 433/89, 90, 226
See application file for complete search history.

(56) References Cited

U.S. PATENT DOCUMENTS

| | | | | | |
|---|---|---|---|---|---|
| 3,195,778 | A | * | 7/1965 | Edwin | 222/80 |
| 3,766,917 | A | * | 10/1973 | Wimmer | 604/88 |
| 4,463,875 | A | * | 8/1984 | Tepic | 222/82 |
| 4,676,655 | A | * | 6/1987 | Handler | 366/130 |
| 4,776,704 | A | * | 10/1988 | Kopunek et al. | 366/184 |
| 5,395,325 | A | * | 3/1995 | Moreno et al. | 604/89 |
| 5,433,705 | A | * | 7/1995 | Giebel et al. | 604/82 |
| 5,496,284 | A | * | 3/1996 | Waldenburg | 604/191 |
| 5,725,500 | A | * | 3/1998 | Micheler | 604/82 |
| 5,779,668 | A | * | 7/1998 | Grabenkort | 604/89 |
| 5,785,683 | A | * | 7/1998 | Szapiro et al. | 604/89 |
| 6,367,962 | B1 | * | 4/2002 | Mizutani et al. | 366/189 |
| 6,488,651 | B1 | * | 12/2002 | Morris et al. | 604/89 |
| 6,544,233 | B1 | * | 4/2003 | Fukui et al. | 604/191 |
| 6,550,957 | B2 | * | 4/2003 | Mizutani et al. | 366/189 |
| 6,981,963 | B2 | * | 1/2006 | Barker et al. | 604/90 |
| 7,018,089 | B2 | * | 3/2006 | Wenz et al. | 366/130 |
| 7,524,103 | B2 | * | 4/2009 | McGill et al. | 366/189 |
| 7,798,363 | B2 | * | 9/2010 | Brandon | 222/1 |
| 7,854,721 | B2 | * | 12/2010 | Peuker et al. | 604/82 |
| 7,905,654 | B1 | * | 3/2011 | Cordero | 366/256 |
| 2004/0122359 | A1 | * | 6/2004 | Wenz et al. | 604/82 |
| 2005/0177100 | A1 | * | 8/2005 | Harper et al. | 604/89 |
| 2011/0004156 | A1 | * | 1/2011 | Keller | 604/82 |

\* cited by examiner

*Primary Examiner* — Victoria P Campbell
(74) *Attorney, Agent, or Firm* — Foley & Lardner LLP

(57) ABSTRACT

A single chamber device for drawing in and dispensing components comprising a syringe housing, a piston that is actuatable by a plunger unit, and a mixing assembly whose rod is guided through the piston and operatively connected to the plunger unit. The plunger unit comprises a plunger rod that is articulated at the mixing rod and provided with means that are engageable with the mixing rod. In this manner, a mixture of different components, particularly also bone cement, can be both created and dispensed in a simple and inexpensive single chamber device.

7 Claims, 3 Drawing Sheets

FIG. 4.1
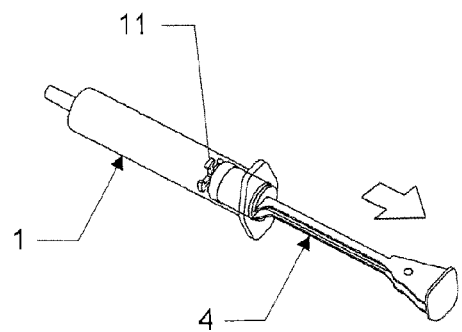
FIG. 4.2
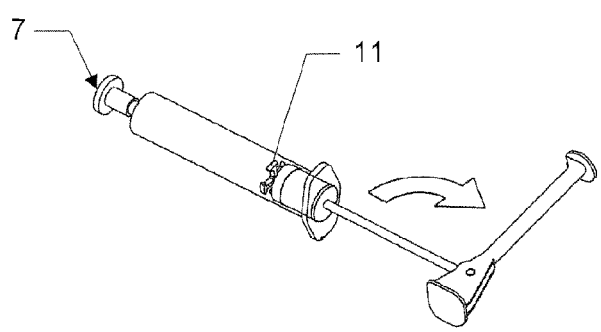
FIG. 4.3
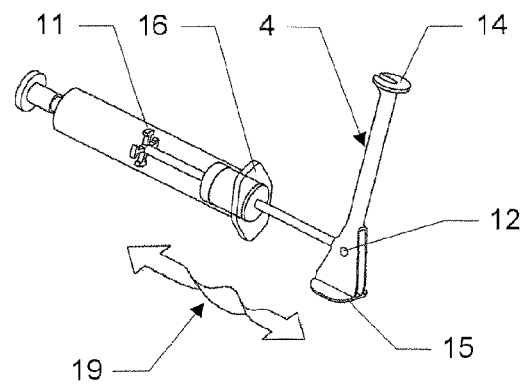
FIG. 4.4
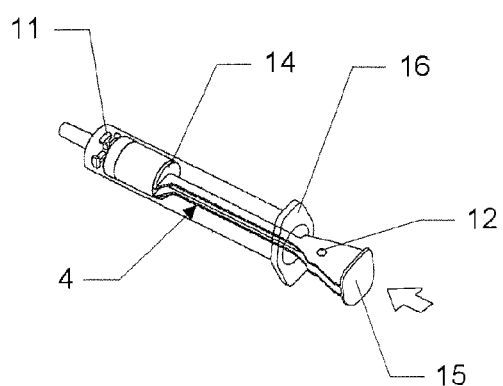

SINGLE CHAMBER DEVICE FOR DRAWING IN AND DISPENSING COMPONENTS

CROSS-REFERENCE TO RELATED PATENT APPLICATIONS

This application claims the benefits of priority to Switzerland Priority Application 0292/08, filed Feb. 28, 2008, and PCT Application PCT/CH2009/000070, filed Feb. 19, 2009, the entire contents of which (including the specification, drawings, claims and abstract) are incorporated herein by reference.

BACKGROUND

The present invention relates to a single chamber device for drawing in and dispensing components according to the preamble of claim 1. Such a device is known from U.S. Pat. No. 3,195,778 where a separate pusher that is driven by the mixing rod has to be inserted for dispensing the mixture.

In the field of medical technique, systems and devices are often required where two or more components in liquid, paste, and/or powder form, such as bone cement, for example, are blended for various applications. The components are generally stored in separate chambers or containers. Particularly in the case of sterile products, the safety with regard to hygiene and the simplicity in the preparation and application are of high importance. Therefore, manually metering, combining, and mixing the components in the open, on one hand, and a complicated handling involving multiple steps in closed systems, on the other hand, should be avoided.

SUMMARY

On the background of this prior art, it is the object of the present invention to improve and simplify a single chamber device for drawing in and dispensing components in such a manner that different components in liquid, paste, or powder form can be brought together and mixed in order to subsequently dispense the resulting mixture by means of the same device.

This object is attained by the device according to claim 1. Further possibilities and advantages of the invention are described in the dependent claims.

BRIEF DESCRIPTION OF THE DRAWINGS

The invention will be explained in more detail hereinafter with reference to drawings of exemplary embodiments.

DETAILED DESCRIPTION

Figure 1:
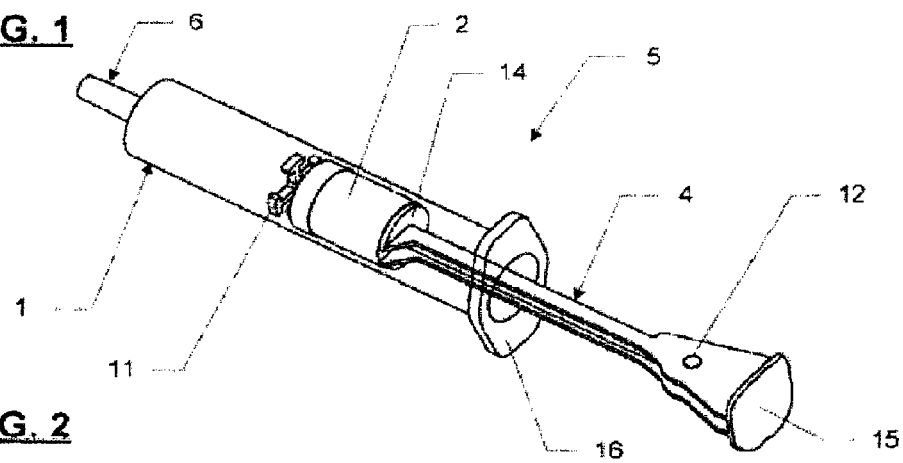
FIG. 1 shows an exemplary embodiment of a device according to the invention in the assembled state.
Figure 2:
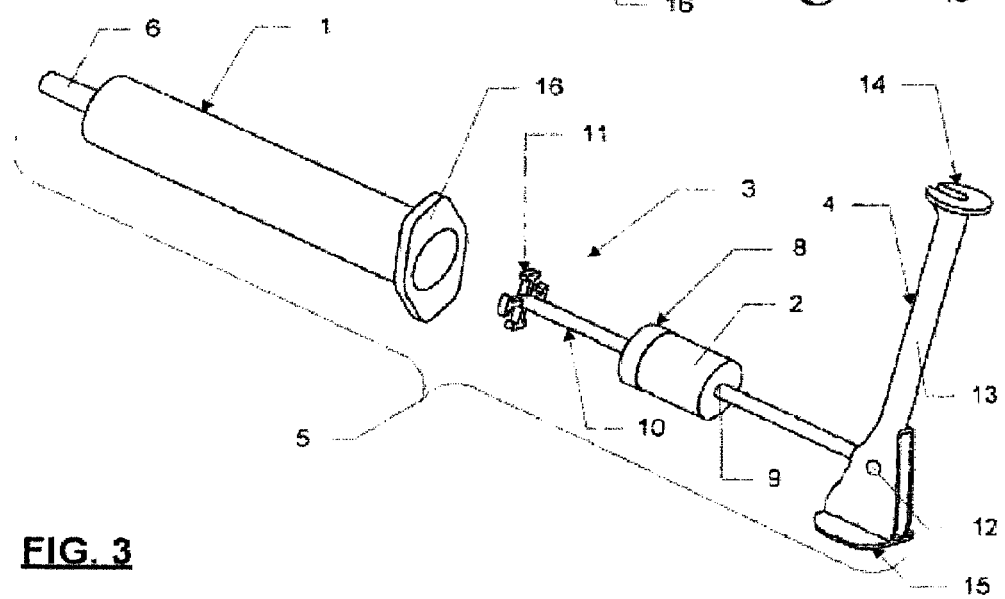
FIG. 2 shows the device of FIG. 1 in an exploded view.

The first exemplary embodiment of the device is described with reference to FIGS. 1 to 5, in particular FIG. 2. Device 5 comprises a syringe housing 1, a piston 2, a mixing assembly 3, and a plunger unit 4. Outlet or inlet 6, respectively, hereinafter called the outlet of syringe 1 is provided with a closure 7 during transport. The dimensions of outlet 6 are standard, e.g. according to the Luer-Lok system.

Piston 2 has is provided with sealing means 8 which both seal its circumference with respect to syringe housing 1 and its passage 9 with respect to mixing rod 10. At the end on the outlet side of mixing rod 10, a mixing disk 11 is arranged, and at its other end, plunger unit 4 is attached via an articulation 12.

In the present embodiment, at one end of plunger rod 13, plunger unit 4 is provided with a flange having a snap recess 14, snap recess 14 being dimensioned so as to catch on mixing rod 10. At the other end of plunger rod 13, a handle with a finger rest 15 is provided, the latter cooperating with retaining flange 16 on syringe housing 1 while the mixture is being dispensed. In order to prevent the piston from being pulled out of the syringe housing, a piston stop 17 is provided at the end of the housing.

Figure 3:
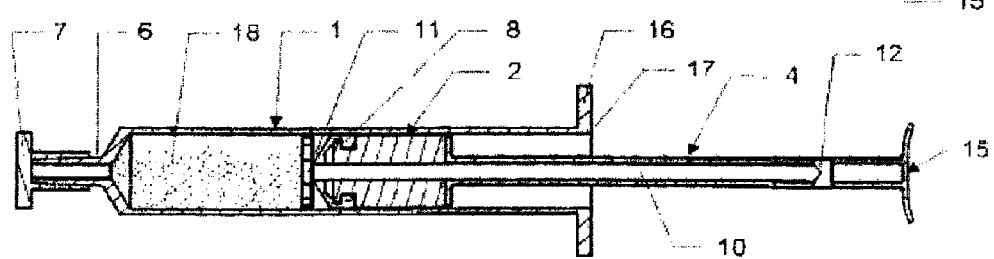
FIG. 3 shows the device of FIG. 1 in a longitudinal section, FIGS. 4.1 to 4.4 schematically show the device of FIG. 1 in different working positions.

In the sectional view of FIG. 3 it is seen that the syringe housing is partly filled with a component, e.g. a powder 18, or a component mixture, such that after the removal of closure 7, the mixing assembly 3 and thus also piston 2 may be retracted by plunger unit 4, thereby allowing a liquid to be drawn or injected into the syringe housing. The sealing means 8 on the piston prevent that the mixture may exit on the other side of the syringe housing.

FIGS. 4.1 to 4.4 and 5 show different working phases in drawing in and mixing the components before they can be dispensed. FIG. 4.1 shows piston 2 with plunger unit 4 in the filled, i.e. retracted position, the plunger rod being engaged to mixing rod 10 by the flange with its snap recess 14, and fully retracted. In the position of FIG. 4.2, the plunger rod has been pivoted by 90° in order to allow the mixing rod to be displaced and rotated without acting upon the piston.

Figure 5:
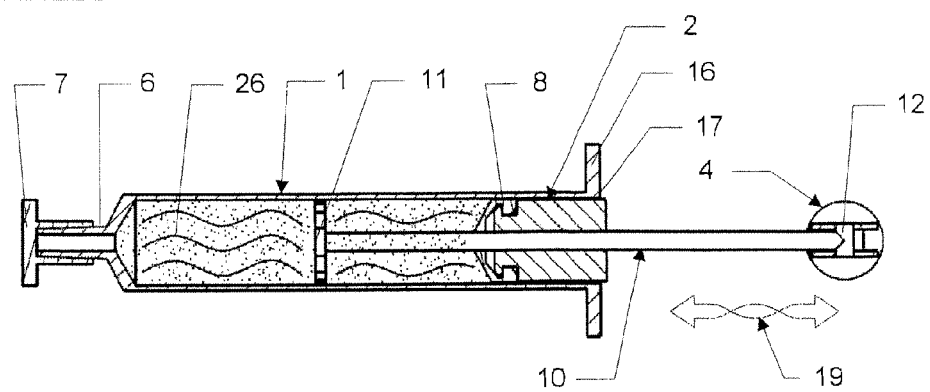
FIG. 5 shows the mixing operation in the device of FIG. 1 in a sectional view.

This longitudinal displacement and simultaneous rotational movement is illustrated in FIG. 4.3 and symbolized by twisted arrow 19. In FIGS. 4.2 and 4.3 it is further seen that the closure has been attached prior to this operation. In the view of FIG. 4.4, the mixing operation has been completed, the plunger rod pivoted back by 90° and snapped onto mixing rod 10 such that the latter may act upon the piston via the flange with its snap recess. Subsequently, by applying pressure to the finger rest, the plunger unit, the piston, and the mixing assembly are pushed toward the outlet in order to dispense the material. In FIG. 5, the mixing operation is again illustrated in a sectional view and symbolized by twisted arrow 19. Of course, prior to dispensing mixture 26, closure 7 is removed.

Figure 6:
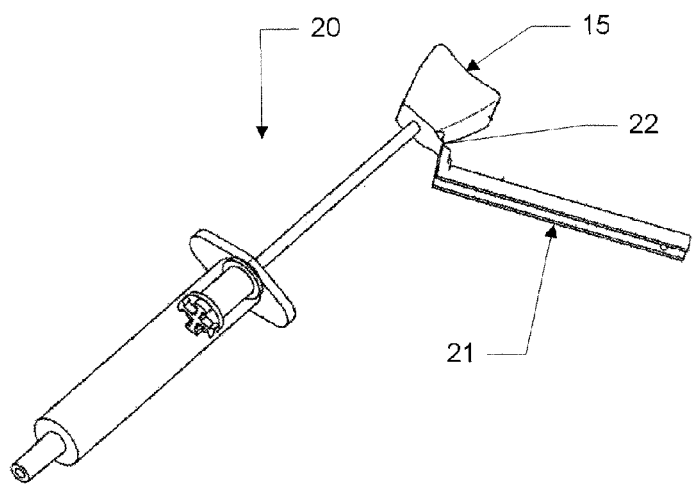
FIG. 6 shows an embodiment variant of the device of FIG. 1.

FIG. 6 shows an embodiment variant of plunger unit 4 where the handle with finger rest 15 of device 20 is arranged on mixing rod 10 and plunger unit 21 is in the form of an articulated part that is connected to the handle via a hinge 22. The function of this plunger unit 21 is the same as in the preceding example, i.e. for the mixing operation, plunger unit 21 is brought to the position of FIG. 7 and for drawing in liquid or ejecting the mixture, the plunger unit is snapped onto mixing rod 10, the plunger rod of this embodiment variant being in the form of a channel section that corresponds to mixing rod 10.

The invention claimed is:

1. A single chamber device for drawing in and dispensing components, comprising:
   a syringe housing;
   a piston that is actuatable by a plunger unit; and
   a mixing assembly whose mixing rod is guided through the piston and operatively connected to the plunger unit,
   wherein the plunger unit includes a plunger rod and the mixing rod further includes a pivot pin at a distal terminus of the mixing rod, wherein the plunger rod is configured to pivot about the pivot pin.

2. The device of claim 1, wherein a first end of the plunger rod includes a flange having a recess that corresponds to the mixing rod and engages the mixing rod.

3. The device of claim 2, wherein a second end of the plunger rod includes a handle with a finger rest.

4. The device of claim 1, wherein the plunger unit is shaped so as to catch on the mixing rod, and wherein the mixing rod includes a handle with a finger rest.

5. The device of claim 1, wherein the piston, arranged in the syringe housing, includes sealing elements, wherein each of the sealing elements seals a circumference of the piston with respect to the syringe housing and a passage of the piston with respect to the mixing rod.

6. The device of claim 1, wherein the mixing assembly includes a mixing disk arranged at an end on an outlet side of the mixing rod.

7. A single chamber device for drawing in and dispensing components, comprising:
   a syringe housing;
   a piston that is actuatable by a plunger unit; and
   a mixing assembly whose mixing rod is guided through the piston and operatively connected to the plunger unit,
   wherein the plunger unit includes:
      a plunger rod that is configured to pivot at the mixing rod, such that during mixing the plunger rod is completely removed from the syringe housing, and
      engaging elements configured to engage the mixing rod.

* * * * *